United States Patent [19]

Oku et al.

[11] Patent Number: 4,626,512

[45] Date of Patent: Dec. 2, 1986

[54] STANDARD SOLUTION FOR SIMULTANEOUSLY CALIBRATING A PLURALITY OF ION ELECTRODES

[75] Inventors: Narihiro Oku; Seiji Usui; Hiroaki Uematsu; Takeshi Kohno, all of Kyoto, Japan

[73] Assignee: Horiba, Ltd., Kyoto, Japan

[21] Appl. No.: 737,036

[22] Filed: May 22, 1985

[30] Foreign Application Priority Data

Jul. 14, 1984 [JP] Japan .................................. 59-146239

[51] Int. Cl.$^4$ ............................................. G01N 31/00
[52] U.S. Cl. ......................................... 436/8; 436/18
[58] Field of Search .................. 436/8, 19; 252/408.1; 23/230 B, 230 R, 938

[56] References Cited

U.S. PATENT DOCUMENTS 4,363,633 12/1982 Christiansen ........................... 436/19

FOREIGN PATENT DOCUMENTS 5635052 6/1979 Japan .

Primary Examiner—John F. Terapane
Assistant Examiner—T. J. Wallen
Attorney, Agent, or Firm—Wenderoth, Lind & Ponack

[57] ABSTRACT

A standard solution for simultaneously calibrating a plurality of ion electrodes for determining a plurality of ion electrodes for determining a plurality of ions including at least potassium ions and calcium ions in blood, the improvement wherein the concentration of the standard solution for a potassium ion electrode and a calcium ion electrode is adjusted in accordance with the following equations:

$$\Delta E = A(\sqrt{\mu} - \sqrt{150})$$

As for potassium ion, $$C = C_0 \cdot 10^{-\Delta E/60}$$

As for calcium ion, $$C = C_0 \cdot 10^{-\Delta E/30}$$

As for potassium ion, $$A = -0.130 \text{ to } -0.065$$

As for calcium ion, $$A = -0.240 \text{ to } -0.172$$

wherein
E: is the potential difference when an ionic strength of 150 mM is used as the standard;
$\mu$: is the ionic strength;
$C_0$: is the calibrated concentration;
C: is the concentration of reagent added; and
A: is the correction factor.

4 Claims, 1 Drawing Figure

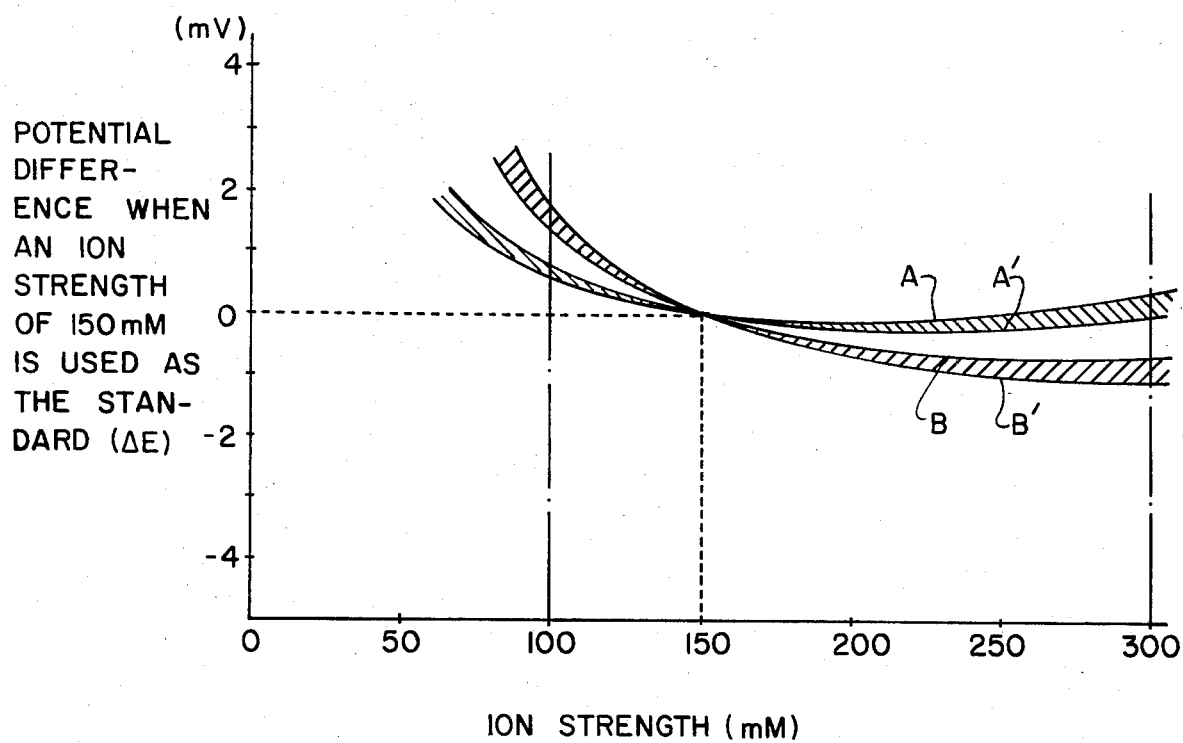

STANDARD SOLUTION FOR SIMULTANEOUSLY CALIBRATING A PLURALITY OF ION ELECTRODES

BACKGROUND OF THE INVENTION

1. Field of the Invention

The present invention relates to a standard solution for simultaneously calibrating a plurality of electrodes for determining the concentrations of a plurality of ions (including at least potassium ions and calcium ions) in blood.

2. Description of the Prior Art

In general, magnesium ions, iron ions, copper ions and the like having an ionic strength of about 150 mM are contained in blood in addition to sodium ions (hereinafter referred to as Na+) of 135 to 145 mM, potassium ions (hereinafter referred to as K+) of 3.5 to 5.0 mM and calcium ions (hereinafter referred to as Ca++) of 1.2 to 1.6 mM. In addition, the pH of blood is 7 to 7.5. Where the concentrations of said ions contained in blood are determined by means of electrodes, it is necessary to calibrate the electrodes periodically by the use of a standard solution which possesses a definite known value for the electrodes, respectively.

When measuring a blood example, it is desirable to carry out the calibration of said electrodes near the ion strength of the ions in the blood sample. The electrodes determine the ionic activity expressed as the product of the concentration and the activity coefficient, which is dependent upon the concentration of the ion to be determined, as well as the concentration of other ions contained in the blood. However, the activity coefficients of ions having equal ion strengths are equal to each other, regardless of the other kinds of ions contained in the blood. Accordingly, where the concentrations of Na+, K+ and Ca++ contained in the blood are determined, it is desirable to calibrate the electrodes by the use of a standard solution of which ion strength is set to about 150 mM.

Although standard solutions for individually calibrating electrodes for determining the Na+, K+, Ca++ or pH is on the market, a standard solution capable of simultaneously calibrating the measurement electrodes corresponding to the above described parameters has never yet been realized. For example, a standard solution merely used for simultaneously calibrating a Ca++ electrode and a pH electrode is disclosed in Japanese Patent Publication unexamined application No. 35062/1981.

SUMMARY OF THE INVENTION

It is an object of the present invention to provide a standard solution for simultaneously calibrating a Na+ electrode, a K+ electrode, a Ca++ electrode and a pH electrode. In particular, the object of the present invention is to provide a standard solution for simultaneously calibrating a plurality of electrodes for determining a plurality of ions (including at least K+ and Ca++) in blood.

The standard solution for simultaneously calibrating a plurality of electrodes according to the present invention is characterized in that the concentration of the standard solution for a potassion ion electrode and a calcium ion electrode are adjusted in accordance with the following equations:

$$\Delta E = A(\sqrt{\mu} - \sqrt{150})$$

As for a potassium ion, $$C = C_o \cdot 10^{-\Delta E/60}$$

As for a calcium ion, $$C = C_o \cdot 10^{-\Delta E/30}$$

As for a potassium ion, $$A: -0.130 \text{ to } -0.065$$

As for a calcium ion, $$A: -0.240 \text{ to } -0.172$$

wherein
- $\Delta E$: is the potential difference when an ion strength of 150 mM (milli mol/l) is used as the standard
- $\mu$: ion strength
- $C_o$: calibrated concentration
- $C$: concentration of a reagent practically added
- $A$: correction factor According to the present invention, in the case where a plurality of different ions are mixed, since the concentrations of K+ and Ca++, which are apt to be influenced by other ions, are adjusted so as to enter within the limits of the shift of potential difference by an ion strength, a standard solution for simultaneously calibrating a plurality of electrodes for determining a plurality of ions including K+ and Ca++ in blood can be obtained in high accuracy. As a result, said electrodes can be calibrated with a high degree of accuracy and certainty.

BRIEF DESCRIPTION OF THE DRAWING

The drawing is a graph showing characteristic curves expressing the relation between a shift of potential difference and the ion strength of K+ and Ca++.

DESCRIPTION OF THE PREFERRED EMBODIMENTS

The standard solution for correctly calibrating the concentration of Na+, K+ or Ca++ in blood calibrating and the value of the pH of the blood by means of the corresponding electrode will be described.

The reagents used for the preparation of the standard solution include sodium chloride (hereinafter referred to as NaCl), potassium chloride (hereinafter referred to as KCl), calcium carbonate (hereinafter referred to as $CaCO_3$), tris(hydroxymethyl)aminomethane [hereinafter referred to as Tris; the chemical formula being $(HOCH_2)_3CNH_2$], hydrochloric acid (hereinafter referred to as HCl) and Triton X-100 [a trade name having the chemical formula $HO(CH_2CH_2O)$—$C_6H_4C_9H_{19}$, i.e. polyethylene glycol mono-p-nonylpheny ether]. It is desirable that these reagents of special or high grade on the market be used.

Preferably, the NaCl, KCl and $CaCO_3$ are used after heating at 110 C. for 6 hours or more to dry and then cooled in a desiccator. HCl is used in the form of a 1 N-solution of which factor was determined beforehand down to three decimal places. In addition, pure water having a conductivity of $1 \times 10^{-7}$ ohm$^{-1}$ cm$^{-1}$ obtained by ion exchange is used in the production of the standard solution.

The concentrations and pH values of the above-described reagents are shown in the two standard solutions described in the following Table 1.

TABLE 1

| Liquid | NaCl (mM) | KCl (mM) | CaCO$_3$ (mM) | HCl (mM) | Tris (mM) | pH (at 37° C.) |
|---|---|---|---|---|---|---|
| Standard solution L Washings | 120 | 4.00 | 1.20 | 37.7 | 50.0 | 7.45 |
| Standard solution H | 200 | 7.10 | 2.55 | 46.5 | 50.0 | 7.10 |

In general, a two-point calibration method (i.e., a high-concentration standard solution and low-concentration standard solution) is used. Hereinafter, a high-concentration standard solution will be referred to as the standard solution H and the low-concentration standard solution will be referred to as the standard solution L.

Both said standard solution L (washings) and said standard solution H contain Triton X-100 in an amount of 10 ppm.

The production procedures of said standard solution L and said standard solution H will be below described together with numerical value as one example thereof. The entire volume of said standard solution is set at 50 liters.

(I) Standard solution L, Washings

A 1 N-HCl (0.995<f<1.005) of 1,885±0.1 ml is added to a mixture of 350.640±0.005 g, NaCl (m.w. 58.44) 14.912±0.001 g of KCl (m.w. 74.56) and 6.005±0.001 g of CaCO$_3$ (m.w. 100.09) in a tank to complete the reaction expressed by the following chemical equation:

$$CaCO_3 + 2HCl \rightarrow CaCl_2 + H_2O + CO_2 \uparrow$$

Then, pure water or distilled water is added to the mixture in said tank to produce a liquid mixture of 30 liters in all. The resulting liquid mixture is sufficiently stirred to dissolve said reagents, whereby a liquid mixture of a uniform concentration is produced.

Then, Tris (m.w. 121.14) of 302.85±0.005 g is dissolved in about 2 liters of pure water to make an aqueous solution of Tris and the resulting aqueous solution of Tris is added to the liquid mixture in said tank with stirring. The reason why Tris is once diluted with pure water is that Tris is alkaline and if added in high concentrations, reacts with said liquid mixture in said tank to produce sediments.

Finally, 5.0 ml of a 10% aqueous solution of Triton X-100 and further pure water is added to make the volume of the liquid mixture 50 liters in all. At this time, the liquid mixture is very easily foamed due to the Triton X-100, so it is necessary to control the stirring.

(II) Standard Solution H

The standard solution H can be produced in the same manner as in the production of said standard solution L described in the above (I) except that said reagents are used in the following quantities:

NaCl (m.w. 58.44)—584.400±0.005 g
KCl (m.w. 74.56)—26.469±0.005 g
CaCO$_3$ (m.w. 100.09)—12.762±0.001 g
1 N-HCl (0.995<f<1.005)—2,325±0.1 ml
Tris (m.w. 121.14)—302.85±0.005 g
Triton X-100 (10% solution)—5.0 ml Although the ion strength of blood is 150 mM as described above, it has been known that a potential difference is produced either when the ion strength is larger than 150 mM or is smaller than 150 mM. The drawing is a graph showing characteristic curves expressing the relation between the ion strengths of K$^+$ and Ca$^{++}$ and the shifts of potential difference, when the ion strength of 150 mM is used as the standard. In the drawing, A, A' is, respectively, the upper limit curve and the lower limit curve for K$^+$ while B, B' is respectively, the upper limit curve and the lower limit curve for Ca$^{++}$.

The present inventors have found that it is necessary to calibrate the concentrations of K$^+$ and Ca$^{++}$ having an ion strength other than the standard ion strength when several kinds of ions are mixed so that the calibration can be carried out in high accuracy by producing a standard solution for the K$^+$ electrode and the Ca$^{++}$ electrode in accordance with the following equations (1) to (5):

$$\Delta E = A ( \sqrt{\mu} - \sqrt{150} ) \quad (1)$$

As for K$^+$:

$$C = C_o \cdot 10^{-\Delta E/60} \quad (2)$$

As for Ca$^{++}$:

$$C = C_o \cdot 10^{-\Delta E/30} \quad (3)$$

As for K$^+$:

$$A = -0.130 \text{ to } -0.065 \quad (4)$$

As for Ca$^{++}$:

$$A = -0.240 \text{ to } -0.172 \quad (5)$$

$\Delta E$ is the potential difference when an ion strength of 150 mM is used as the standard, $\mu$ is the ion strength, $C_o$ is the calibrated concentration, C is the concentration of the reagent added, and A is a correction factor.

The standard solution L produced in (I) above is shown in the following Table 2, while the standard solution H produced in (II) above is shown in the following Table 3:

TABLE 2

| Calibrated conc. | | Reagent used | Conc. of reagent |
|---|---|---|---|
| Na$^+$ | 120 mM | NaCl | 120 mM |
| K$^+$ | 4 mM | KCl | 4 mM |
| Ca$^{++}$ | 1.2 mM | CaCO$_3$ | 1.2 mM |
| pH | 7.45 (at 37° C.) | Tris | 50 mM |
| | | HCl | 37.7 mM |
| Ion Strength | | | 165.5 mM |

TABLE 3

| Calibrated conc. | | Reagent used | Conc. of reagent |
|---|---|---|---|
| Na$^+$ | 200 mM | NaCl | 200 mM |
| K$^+$ | 7 mM | KCl | 7.1 mM |
| Ca$^{++}$ | 2.4 mM | CaCO$_3$ | 2.55 mM |
| pH | 7.10 (at 37° C.) | Tris | 50 mM |
| | | HCl | 46.6 mM |

TABLE 3-continued

| Calibrated conc. | Reagent used | Conc. of reagent |
|---|---|---|
| Ion strength | | 261.35 mM |

In the production of a standard solution in accordance with said equations (1) to (5), at first the ionic strength $\mu$ is calculated from a calibrated concentration, the value of $\mu$ being put into said equation (1) to determine $\Delta E$, and the value of $\Delta E$ being put into said equations (2), (3) to determine C of $K^+$ and $Ca^{++}$, respectively.

For example, when the calibrated concentration is 200 mM for $Na^+$, 7 mM for $K^+$, 2.4 mM for $Ca^{++}$, 50 mM for Tris, and 46.6 mM for HCl (pH: 7.10), respectively, the ionic strength $\mu$ is 258.4 mM. If this value of $\mu$ is put into the equation (1), $$\Delta E = A \times (\sqrt{258.4} - \sqrt{150}) = A \times 3.83$$

holds good.

Here, provided that A is $-0.130$ to $-0.065$ for $K^+$ and $-0.240$ to $-0.172$ for $Ca^{++}$, respectively, said values are put into the equations (2) and (3) to obtain $\Delta E = -0.50$ to $-0.25$, C=7.067 to 7.135 for $K^+$ and $\Delta E = -0.92$ to $-0.66$, C=2.525 to 2.576 for $Ca^{++}$.

Although the values of C and $K^+$ and $Ca^{++}$ obtained in the above described manner ought to enter between said upper limit curve and said lower limit curve shown in the drawing, the calibrating operation, wherein the ionic strength $\mu$ is calculated from the obtained value of C, the value of $\mu$ being put into the equation (1) to obtain $\Delta E$, and the value of $\Delta E$ being put into the equations (2) and (3) to obtain C, should be carried out one or more times.

For example, in the above described example, the following results are obtained:

| Before the calibration | | After the calibration | |
|---|---|---|---|
| $Na^+$: | 200 mM | $Na^+$: | 200 mM |
| $K^+$: | 7 mM | $K^+$: | 7.06 to 7.14 mM |
| $Ca^{++}$: | 2.4 mM | $Ca^{++}$: | 2.52 to 2.58 mM |
| pH: | 7.10 | pH: | 7.10 |
| (Tris: | 50 mM | (Tris: | 50 mM, |
| HCl: | 46.6 mM) | HCl: | 46.6 mM) |
| $\mu$ = 258.4 | | $\mu$ 258.7 to 258.9 | |

It will be understood also from the above described Example that the ionic strength is slightly changed. In addition, also the value of the pH is changed, and therefore, it is necessary to somewhat change the quantity of HCl according to circumstances in order to calibrate this change. Accordingly, the calibration may be carried out again on the basis of the calibrated ionic strength. However, such a change is, in fact, within the ordinary and acceptable range, so it does not become a practical or major problem.

What is claimed is:

1. A standard solution for simultaneously calibrating a plurality of ion electrodes for determining a plurality of ions, which includes at least potassium ions and calcium ions in blood, said standard solution consisting essentially of an aqueous solution of sodium chloride, potassium chloride, calcium carbonate, Tris(hydroxy)aminomethane and hydrochloric acid, wherein the concentration of the standard solution for the potassium ion electrode and the calcium ion electrode is adjusted in accordance with the following equations:

$$\Delta E = A(\sqrt{\mu} - \sqrt{150})$$

potassium ions:

$$C = C_o \cdot 10^{-\Delta E/60}$$

calcium ions:

$$C = C_o \cdot 10^{-\Delta E/30}$$

potassium ions:

$$A = -0.130 \text{ to } -0.065$$

calcium ions:

$$A = -0.240 \text{ to } -0.172$$

wherein
$\Delta E$: is the potential difference when an ionic strength of 150 mM is used as the standard;
$\mu$: is the ionic strength;
$C_o$: is the calibrated concentration;
C: is the concentration of reagent added; and
A: is the correction factor.

2. A standard solution according to claim 1 wherein the solution also contains a polyethylene glycol mono-p-nonylphenyl ether.

3. A standard solution according to claim 2 wherein the hydrochloric acid is present as a 1 N-solution.

4. A standard solution according to claim 1 used for simultaneously calibrating an $Na^+$ electrode, a $K^+$ electrode, a $Ca^{++}$ electrode, and a pH electrode.

* * * * *